United States Patent [19]
Mak

[11] Patent Number: 5,684,222
[45] Date of Patent: Nov. 4, 1997

[54] MUTANT MOUSE HAVING A DISRUPTED TNFRP55

[75] Inventor: Tak W. Mak, Toronto, Canada

[73] Assignee: Ontario Cancer Institute, Toronto, Canada

[21] Appl. No.: 274,122

[22] Filed: Jul. 12, 1994

Related U.S. Application Data

[63] Continuation of Ser. No. 8,579, Jan. 22, 1993, abandoned.
[51] Int. Cl.$^6$ .......................... A61K 31/00; C12N 5/06; C12N 15/06; C12N 15/85
[52] U.S. Cl. .................... 800/2; 424/9.2; 435/172.3; 435/240.21; 800/DIG. 1; 800/DIG. 2
[58] Field of Search ................................ 800/2, DIG. 1, 800/DIG. 2; 435/69.2, 172.1, 172.3, 240.1, 240.2, 240.21

[56] References Cited

PUBLICATIONS

Ashkenazi et al., "Protection against endotoxic shock by a tumor necrosis factor receptor immunoadhesin", *Proc. Natl. Acad. Sci. USA* 88:10535–10539 (1991).

Baeuerle, "The inducible transcription activator NF–κB: regulation by distinct protein subunits", *Biochimica et Biophysica Acta* 1072:63–80 (1991).

Beutler et al., "The Biology of Cachectin/TNF—A Primary Mediator of the Host Response", *Ann. Rev. Immunol.* 7:625–655 (1989).

Buetler et al., "Passive Immunization Against Cachectin/ Tumor Necrosis Factor Protects Mice from Lethal Effect of Endotoxin", *Science* 229:869–871 (1985).

Bradley et al., "Embryo–Derived Stem Cells: A Tool for Elucidating the Developmental Genetics of the Mouse", *Current Topic in Developmental Biology* 20:357–371 (1986).

Camerini et al., "The T Cell Activation Antigen CD27 is a Member of the Nerve Growth Factor/Tumor Necrosis Factor Receptor Gene Family", *The Journal of Immunology* 147(9):3165–3169 (1991).

Capecchi, "Altering the Genome by Homologous Recombination", *Science* 244:1288–1292 (1989).

de Kossodo et al., "Tumor Necrosis Factor α is Involved in Mouse Growth and Lymphoid Tissue Development", *J. Exp. Med.* 176:1259–1264 (1992).

Giroir et al., "Constitutive synthesis of tumor necrosis factor in the thymus", *Proc. Natl. Acad. USA* 89:4864–4868 (1992).

Giroir et al., "The Tissue Distribution of Tumor Necrosis Factor Biosynthesis During Endotoxemia", *J. Clin. Invest* 90:693–698 (1992).

(List continued on next page.)

*Primary Examiner*—Brian R. Stanton
*Attorney, Agent, or Firm*—Marshall, O'Toole, Gerstein, Murray & Borun

[57] ABSTRACT

The multiple biological activities of tumor necrosis factor (TNF) are mediated by two distinct cell surface receptors of 55 and 75 kDa. Mutant mice of the invention lacking tumor necrosis factor receptor (TNFR) p55 still express functional TNFRp75 molecules at the cell surface. Normal weight and size of the mutant mice are not altered. Thymocyte development and lymphocyte populations are normal, and clonal deletion of potentially self-reactive T cells is not impaired. Activation of the nuclear transcription factor κB (NF-κB), however, is completely abrogated after stimulation with TNF. Moreover, TNFRp55 mutant mice are protected from septic shock induced by bacterial endotoxin or superantigen, but Listeria clearance is severely impaired and mutant mice easily succumb to Listeria infection. Thus, the two TNF receptors are not redundant, are independently controlled, and play different roles in normal and pathological physiology.

7 Claims, 9 Drawing Sheets

PUBLICATIONS

Goodwin et al., "Molecular Cloning and Expression of the Type 1 and Type 2 Murine Receptors for Tumor Necrosis Factor", *Molecular and Cellular Biology* 11(6):3020–3026 (1991).

Gray et al., "Cloning of human tumor necrosis factor (TNF) receptor cDNA and expression of recombinant soluble TNF–binding protein", *Proc. Natl. Acad. Sci. USA* 87:7380–7384 (1990).

Himmler et al., "Molecular Cloning and Expression of Human and Rat Tumor Necrosis Factor Receptor Chain (p60) and Its Soluble Derivative, Tumor Necrosis Factor-Binding Protein", *DNA and Cell Biology* 9(10):705–715 (1990).

Lee et al., "Targeted Mutation of the Gene Encoding the Low Affinity NGF Receptor p75 Leads to Deficits in the Peripheral Sensory Nervous System", *Cell* 69:737–749 (1992).

Lewis et al., "Cloning and expression of cDNAs for two distinct murine tumor necrosis factor receptors demonstrate one receptor is species specific", *Proc. Natl. Acad. Sci. USA* 88:2830–2834 (1991).

Loetscher et al., "Molecular Cloning and Expression of the Human 55 kd Tumor Necrosis Factor Receptor", *Cell* 61:351–359 (1990).

Mallett et al., "A new superfamily of cell surface proteins related to the nerve growth factor receptor", *Immunology Today* 12(7):220–223 (1991).

Mansour, "Gene Targeting in Murine Embryonic Stem Cells: Introduction of Specific Alterations into the Mammalian Genome", *GATA* 7(8):219–227 (1990).

Miethke et al., "T Cell–mediated Lethal Shock Triggered in Mice by the Superantigen Staphylococcal Enterotoxin B: Critical Role of Tumor Necrosis Factor", *J. Exp. Med.* 175:91–98 (1992).

Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor", *The EMBO Journal* 9:3269–3278 (1990).

Ohsawa et al., "Expression of Tumor Necrosis Factor at a Specific Developmental Stage of Mouse Embryos", *Developmental Biology* 135:459–461 (1989).

Pfeffer et al., "Mice Deficient for the 55 kd Tumor Necrosis Factor Receptor are Resistant to Endotoxic Shock, yet Succumb to *L. monocytogenes* Infection", *Cell* 73:457–467 (1993).

Robertson, "Using Embryonic Stem Cells to Introduce Mutations into the Mouse Germ Line", *Biology of Reproductions* 44:238–245 (1991).

Schall et al., "Molecular Cloning and Expression of a Receptor for Human Tumor Necrosis Factor", *Cell.* 61:361–370 (1990).

Smith et al., "A Receptor for Tumor Necrosis Factor Defines an Unusual Family of Cellular and Viral Proteins", *Science* 248:1019–1023 (1990).

Tartaglia et al., "Two TNF receptors", *Immunology Today*, 13(5):151–153 (1992).

Thomas et al., "Identification of a 60–kD Tumor Necrosis Factor (TNF) Receptor as the Major Signal Transducing Component in TNF Responses", *J. Exp. Med.* 172:1019–1023 (1990).

Thomas et al., "Site–Directed Mutagenesis by Gene Targeting in Mouse Embryo–Derived Stem Cells", *Cell* 51:503–512 (1987).

Tracey et al., "Anti–cachectin/TNF monoclonal antibodies prevent septic shock during lethal bacteraemia", *Nature* 330:662–664 (1987).

Tracey et al., "Shock and Tissue Injury Induced by Recombinant Human Cachectin", *Science* 234:470–474 (1986).

Wiegmann et al., "Human 55–kDa Receptor for Tumor Necrosis Factor Coupled to Signal Transduction Cascades", *J. Biol. Chem.* 267(25):17997–18001 (1992).

Goodwin et al. 1991. Molecular and Cellular Biology 11(6):3020–3026.

Camerini et al. 1991. J. Immunol. 147(9):3165–3169.

Lee et al 1992. Cell 69:737–749.

Monsour et al 1990. Gene Analysis Tech Appl. (GATA) 7(8):219–227.

Robertson 1991 Biol. Rerod. 44:238–245.

TNFRp55 +/+

Fig. 5A

TNFRp55 -/-

MUTANT MOUSE HAVING A DISRUPTED TNFRP55

This application is a continuation of application Ser. No. 08/008,579, filed Jan. 22, 1993, now abandoned.

Tumor necrosis factor α (TNFα) and TNFβ (lymphotoxin) affect the growth, differentiation, and function of a multitude of cell types and are mediators in inflammation and cellular immune responses (Beutler and Cerami, 1988; Beutler and Cerami, 1989; Old, 1988; Paul and Ruddle, 1988; Vassalli, 1992). TNFα was originally identified due to its antitumoral and cachexia inducing activities (Beutler and Cerami, 1988; Beutler and Cerami, 1989). In the mouse, constitutive expression of TNFα can be detected in thymocytes (Giroir et al., 1992). TNFα expression is readily induced after administration of bacterial endotoxin (lipopolysaccharide, LPS) in macrophages, kidney, heart, endocrine pancreas, spleen, lung, fallopian tubes, and uterus (Giroir et al., 1992). High dose challenge with either LPS or bacterial superantigens leads to a septic shock syndrome which is mediated by TNF released from macrophages or T cells, respectively (Morrison and Ryan, 1987; Tracey et al., 1986; Miethke et al., 1992). Protection against lethal toxicity can be conferred by passive immunisation with anti-TNF antiserum or with recombinant soluble human TNF receptor-Ig chimeric proteins (Tracey et al., 1987; Beutler et al., 1985; Miethke et al., 1992; Ashkenazi et al., 1991). In contrast to the detrimental effects of TNF in septic shock, TNF also appears to increase host defense in cell-mediated immunity against obligate and facultative intracellular bacteria and parasites (Nakane et al., 1988; Nakane, 1992). Protection against *Listeria monocytogenes*, a facultative intracellular gram-positive coccobacillus, can be effectively supported by TNF, while anti-TNF antibodies impair the ability of mice to cope with this infection (Nakane, 1992).

The potent regulatory abilities of TNFα and TNFβ are transduced by two distinct receptors on the cell surface that have molecular weights of 55 kDa and 75 kDa. Both receptor species have been molecularly cloned in man (Schall et al., 1990; Smith et al., 1990; Thoma et al., 1990; Loetscher et al., 1990; Nophar et al., 1990; Gray et al., 1990; Himmler et al., 1990) and mouse (Goodwin et al., 1991; Lewis et al., 1991). In the mouse TNFRp55 and TNFRp75 have been mapped to chromosome 6 and 4, respectively (Goodwin et al., 1991). The $K_d$ values of TNFRp55 and TNFRp75 for mTNFα are approximately 200 pM and 50 pM, respectively (Lewis et al., 1991). Both receptor chains also bind TNFβ with high affinity (Goodwin et al., 1991; Lewis et al., 1991). The extracellular domains of TNFRp55 and TNFRp75 share 28% identity and are characterised by four repeated cysteine-rich motifs with significant intersubunit sequence homology (Tartaglia and Goeddel, 1992). These properties are shared by a family of diverse cell surface proteins, including nerve cell growth factor receptor, Fas antigen, Bp50, Ox40, CD27, CD30 and CD40 (Tartaglia and Goeddel, 1992; Mallett and Barclay, 1991). Interestingly, some viruses contain genes coding for secreted proteins with TNF binding affinity which are closely homologous to TNFRp55 and TNFRp75 (reviewed in Mallett and Barclay, 1991).

The intracytoplasmic domains of the two TNF receptor chains are not homologous and may generate different signals. Potential intracytoplasmic regions of TNF receptor chains important for signaling might be the carboxyterminal half of the p55 chain and a number of conserved serine residues which appear to be targets for phosphorylation in the p75 chain (Tartaglia and Goeddel, 1992; Goodwin et al., 1991; Lewis et al., 1991). Currently, in vitro studies suggest that the two receptors signal distinct activities, e.g. TNFRp55 has been implicated with cytotoxicity, antiviral activity, and fibroblast proliferation; whereas, TNFRp75 seems to be involved in thymocyte and T cell proliferation (for review see Tartaglia and Goeddel, 1992).

Increasing evidence suggests that induction of NF-κB is crucial for the activation of a set of TNF-responsive genes. NF-κB controls the expression of a set of cellular and viral genes and was originally described as being present in the cytosol of most cell types as an inactive heterodimer composed of 50 kd (p50) and 65 kd (p65) subunits which are bound to a cytoplasmic inhibitor protein or protein complex (I-κB) (Baeuerle, 1991). Dissociation from I-κB allows nuclear translocation of the p50-p65 heterodimer with consecutive binding to cognate DNA sequences. TNFRp55 is involved in triggering second messenger systems such as phospholipase $A_2$, protein kinase C, Phosphatidylcholine specific-phospholipase C (PC-PLC), and Sphingomyelinase (SMase) (Schutze et al., 1992). Induction of nuclear NF-κB activity has recently been shown to be critically dependent on the generation of sphingomyelin by an acidic SMase. SMase activation is secondary to the production of 1,2-diacylglycerol by a TNFRp55-responsive PC-PLC (Schutze et al., 1992). Only little is known about the signal events mediated by TNFRp75 (Tartaglia and Goeddel, 1992).

The present invention provides a mutant mammal mouse, having a disrupted TNFRp55 gene. The invention is useful for understanding the multitude of TNF effects in vivo and the role of each of the receptors. Farther reaching therapeutic utility of the invention will be apparent to the skilled person. The TNFRp55 gene was targeted in embryonic stem cells and mice homozygous for this mutation were generated (Bradley and Robertson, 1986; Bradley et al., 1984; Fung-Leung et al., 1991; Thomas and Capecchi, 1987; Thompson et al., 1989). TNFRp55–/– mice lack the ability to bind human TNFα but are still able to bind mouse TNFα, indicating that the TNFRp75 chain can be functionally expressed at the cell surface without TNFRp55. Mutant mice appear normal with regard to development, weight and organ sizes. Strikingly, while TNFRp55 mutant mice do not succumb to LPS-induced and superantigen-induced toxicity, they cannot mount a protective immune response against Listeria. TNF-inducible nuclear expression of NF-κB is completely absent in TNFRp55–/– mice. These findings indicate that TNFRp55 is obligate for toxicity of TNF and TNFRp55 is highly important for host defense, and thus, suggests that the two TNF receptors mediate dissimilar functions in normal and pathological physiology.

TARGETING OF TNFRp55

Figure 1A:
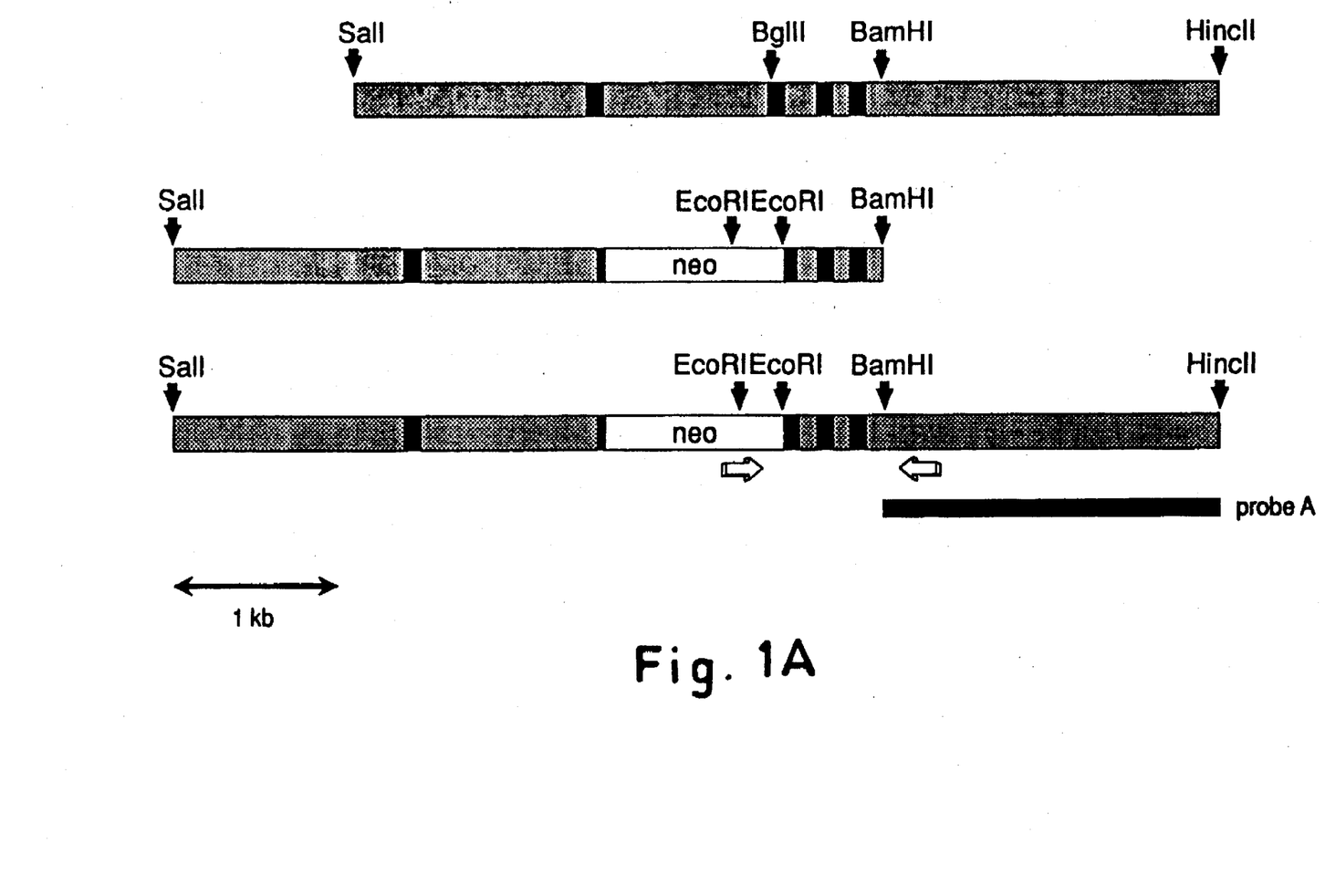
FIG. 1A is a schematic diagram of the targeting strategy for disruption of the TNFRp55 gene.
Figure 1B:
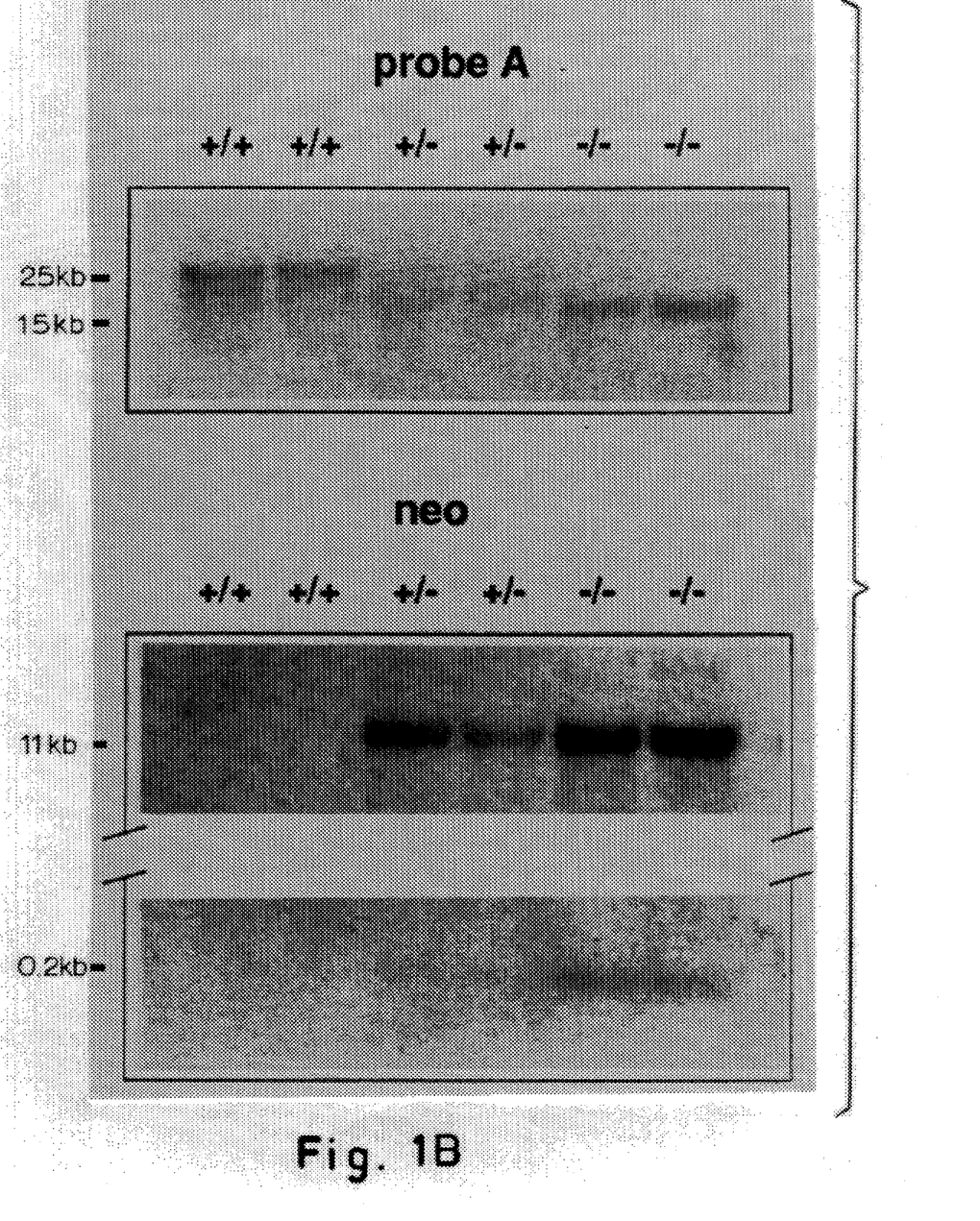
FIG. 1B shows Southern blots of resistant colonies screened by PCR confirming homologous recombination.

The TNFRp55 targeting vector (FIG. 1A) was constructed from a 3.2 kB DNA fragment derived from a genomic clone isolated from a Balb/C EMBL3 library. The coding sequence was disrupted by insertion of a neomycin-resistance gene cassette (neo) derived from pMCIpolA (Thomas and Capecchi, 1987) using a BglII restriction site. This DNA construct was introduced into D3 embryonic stem cells by electroporation and subjected to G418 selection. Resistant colonies were screened by PCR (infra) and homologous recombination was confirmed by Southern analysis (FIG. 1B). Of 1024 colonies tested, 2 contained the mutation. Both clones were injected into C57BL/6 blastocysts, and the embryos were reimplanted into foster animals. Chimeric mice derived from both clones transmitted the mutation to offspring. Heterozygotes were intercrossed to generate TNFRp55–/– homozygotes. The F2 animals were bred under germ-free conditions. Male and female homozygous mice are fertile and appear healthy upon observation up to 10 months of age.

TNFRp55 deficient mice still express TNFRp75

Figure 2:
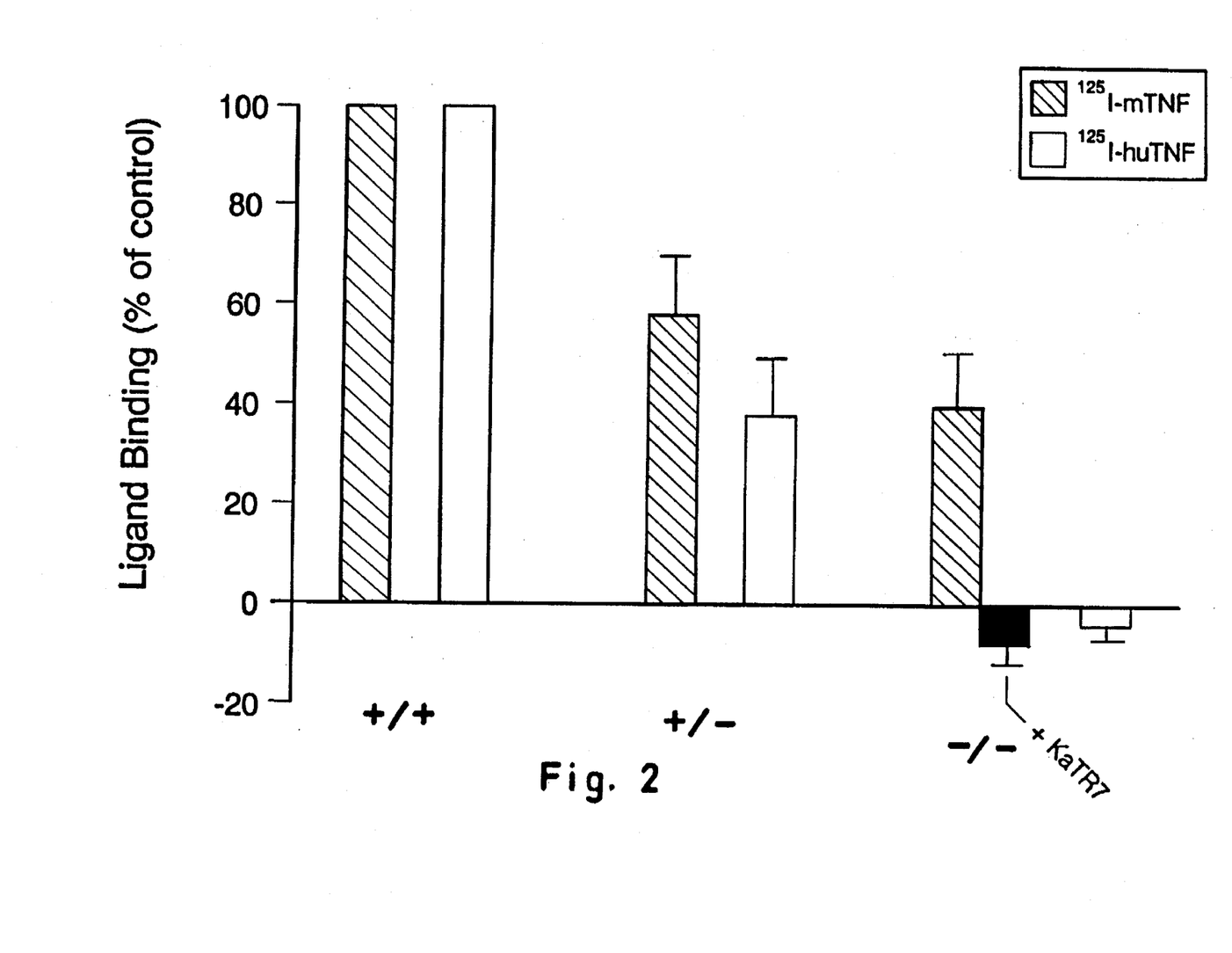
FIG. 2 is a graph showing binding of mouse and human TNFα by various mouse strains.

Cell surface expression of TNF receptors was tested using a sensitive radioligand binding assay. It has been reported that mouse TNFRp55 also binds human TNFα with high affinity, whereas mouse TNFRp75 has a very low or almost undetectable affinity for human TNFα (Goodwin et al., 1991). Binding of mouse and human $^{125}$I-TNFα was examined on ConA stimulated spleen cells. As shown in FIG. 2, spleen cells derived from TNFRp55+/+ and TNFRp55+/– mice bound mouse and human TNFα. However, only mouse TNFα but not human TNFα binding could be detected on TNFRp55–/– spleen cells, indicating that TNFRp75 is still detectable on the cell surface. The binding capacity of TNFRp55–/– cells for mouse TNFα could be completely blocked by the rat anti-mouse TNFRp75 monoclonal antibody (mAb) KaTR7, raised against a mouse TNFRp75/Glutathione fusion protein. These data indicate that mice homozygous for the mutation of TNFRp55 do not express TNFRp55 on the cell surface and cell surface expression of TNFRp75 is independent of TNFRp55 on splenocytes.

Abrogation of NF-κB-activation

Figure 3:
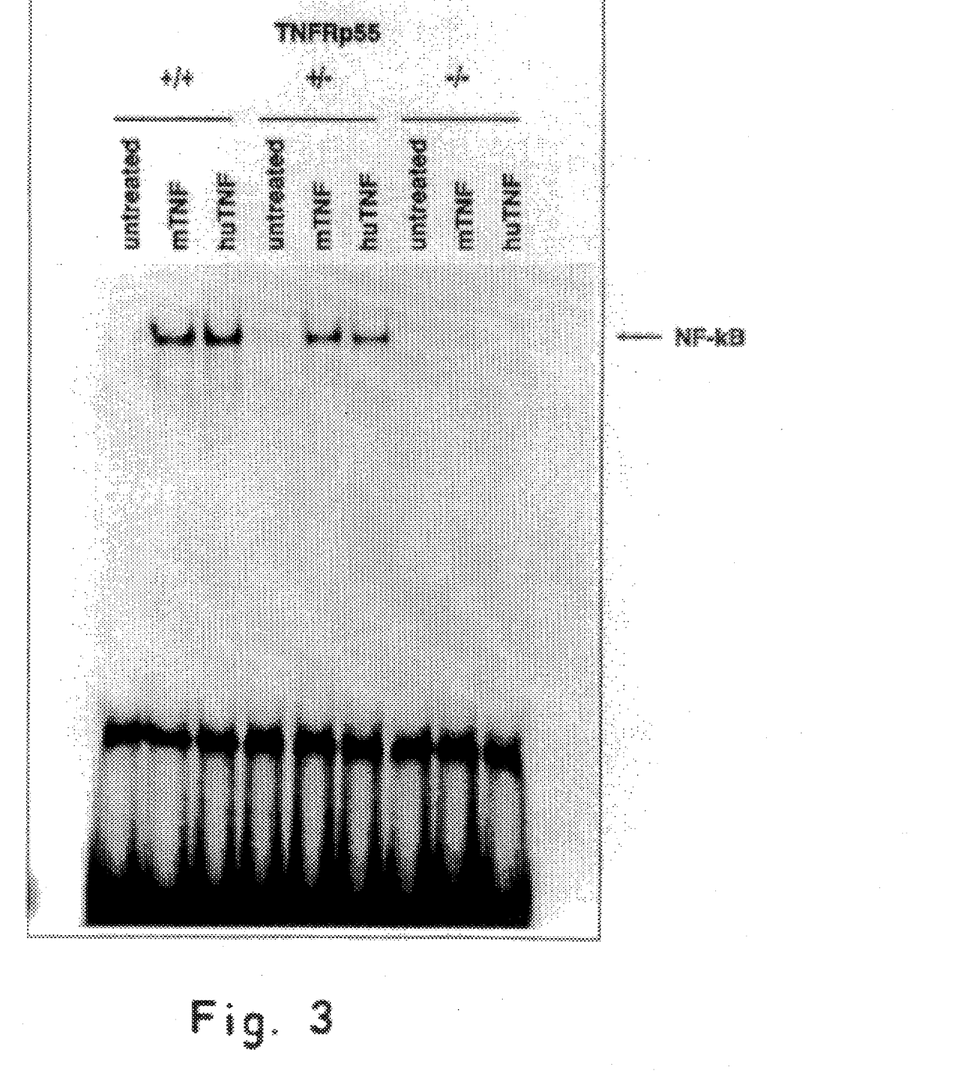
FIG. 3 is an electrophoretic mobility shift assay analyzing for NF-κB binding capacity of nuclear extracts from various mouse strains both with and without prior TNFα stimulation.

Induction of NF-κB involves dissociation of NF-κB from a cytosolic inhibitor protein or protein complex (I-κB) with consecutive translocation to the nucleus (Baeuerle, 1991). On human cell lines, huTNFα and agonistic antibodies to TNFRp55 have been shown to activate NF-κB (Tartaglia and Goeddel, 1992). Analysis of NF-κB induction in TNFRp55 deficient mice was performed by electrophoretic mobility shift assay. Spleen cells of TNFRp55+/+, TNFRp55+/– and TNFRp55–/– mice were grown in the presence of ConA. After 6 days cells were stimulated with nil, human TNFα or mouse TNFα. Nuclear extracts were prepared and analyzed for NF-κB binding capacity by electrophoretic mobility shift assay (FIG. 3). Mouse and human TNFα triggered NF-κB activation in wildtype and heterozygous mice, while the retarded complex could not be detected after stimulation with human or mouse TNFα in TNFRp55 mutant mice. This result indicates that activation of NF-κB is completely dependent upon TNFRp55 signaling.

TNFRp55 deficient mice delete I-E and Mls1$^a$ reactive T cells

Figure 4A:
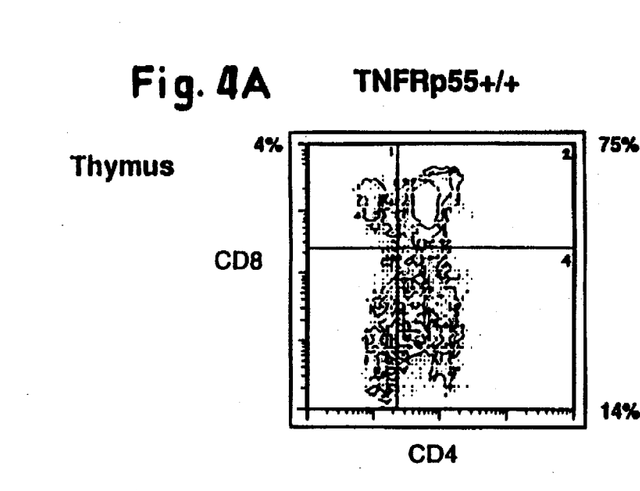
FIGS. 4A–4D show fluorescence cell activator staining (FACS) of thymocytes from +/+ (FIG. 4A) and –/– (FIG. 4B) mice, and B cells from +/+ (FIG. 4C) and –/– (FIG. 4D) mice as analyzed by B220 staining.
Figure 4B:
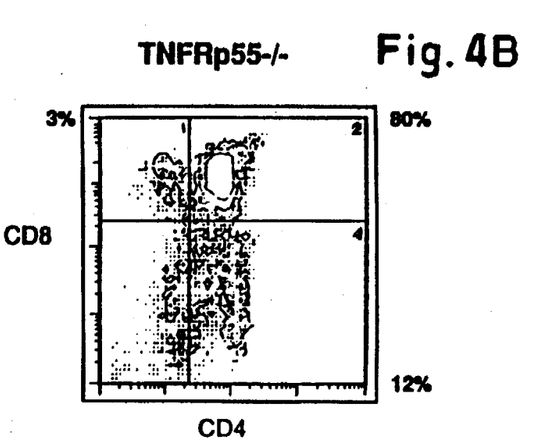
Figure 4C:
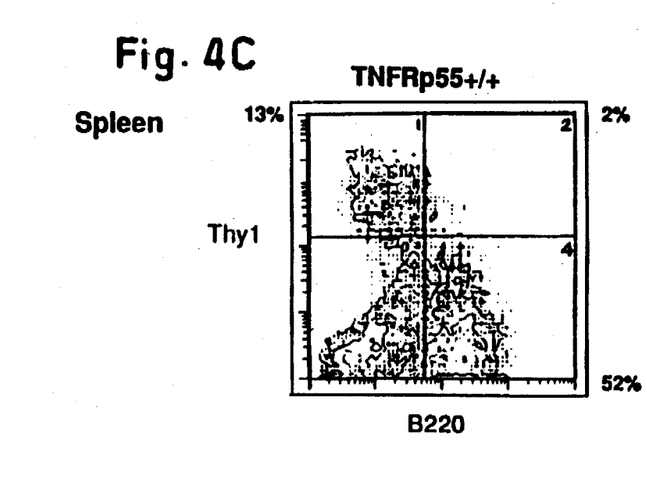
Figure 4D:
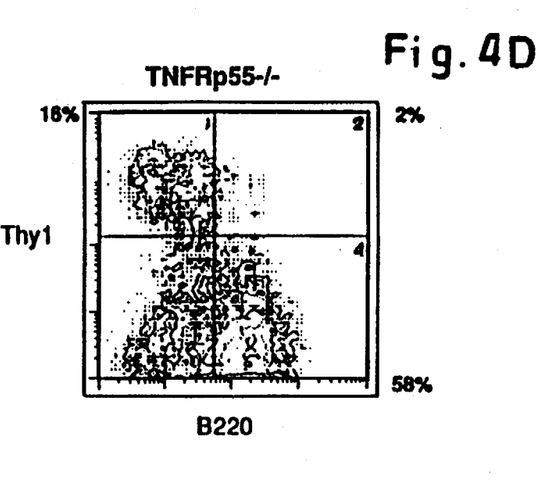
Figure 5A:
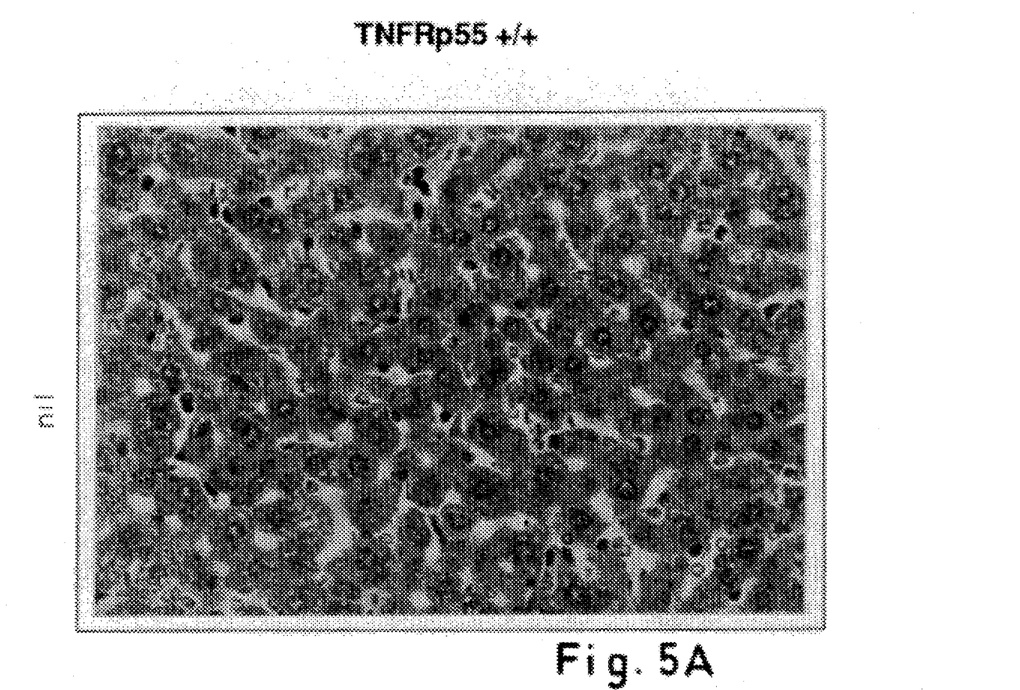
FIGS. 5A–5H show staining of liver tissue sections of +/+ and –/– mice after administration of LPS and D-Gal (FIG. 5C and FIG. 5D, respectively), LPS (FIG. 5E and FIG. 5F, respectively), D-Gal (FIG. 5G and FIG. 5H, respectively) as compared to control (nil) tissues (FIG. 5A and FIG. 5B, respectively).
Figure 5B:
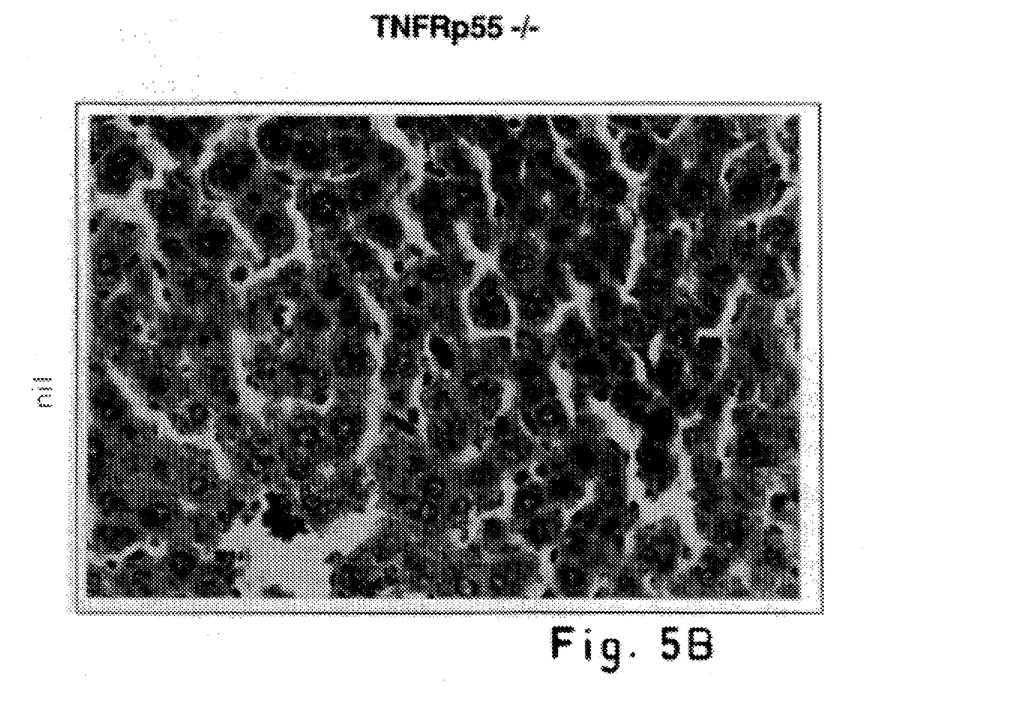
Figure 5C:
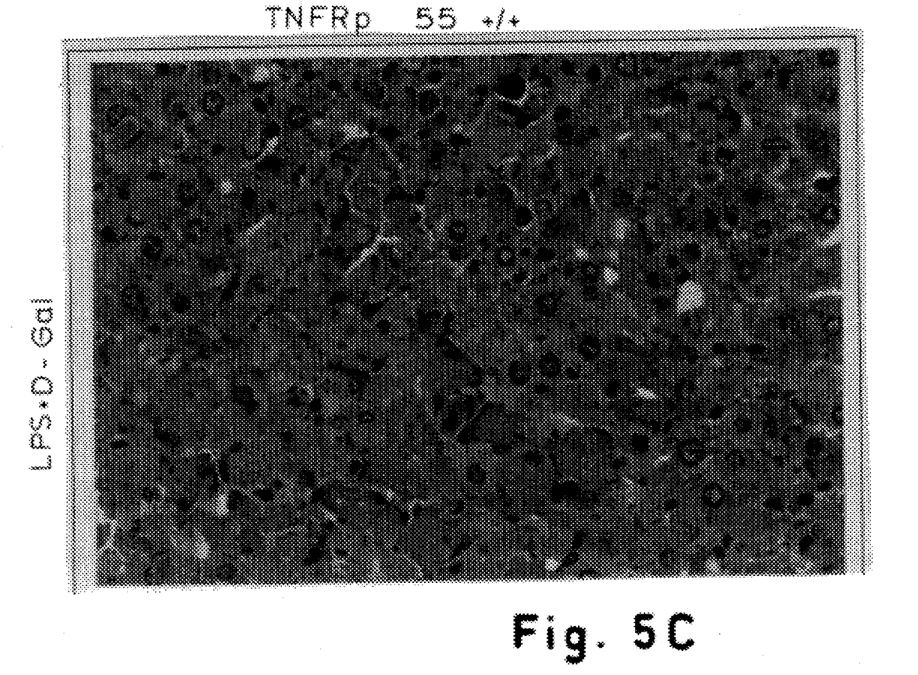
Figure 5D:
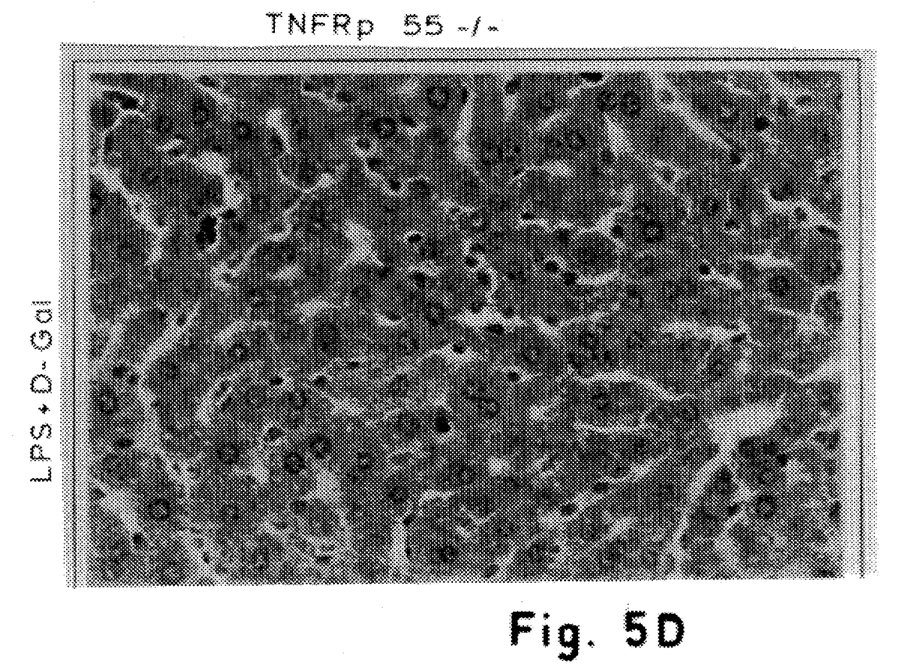
Figure 5E:
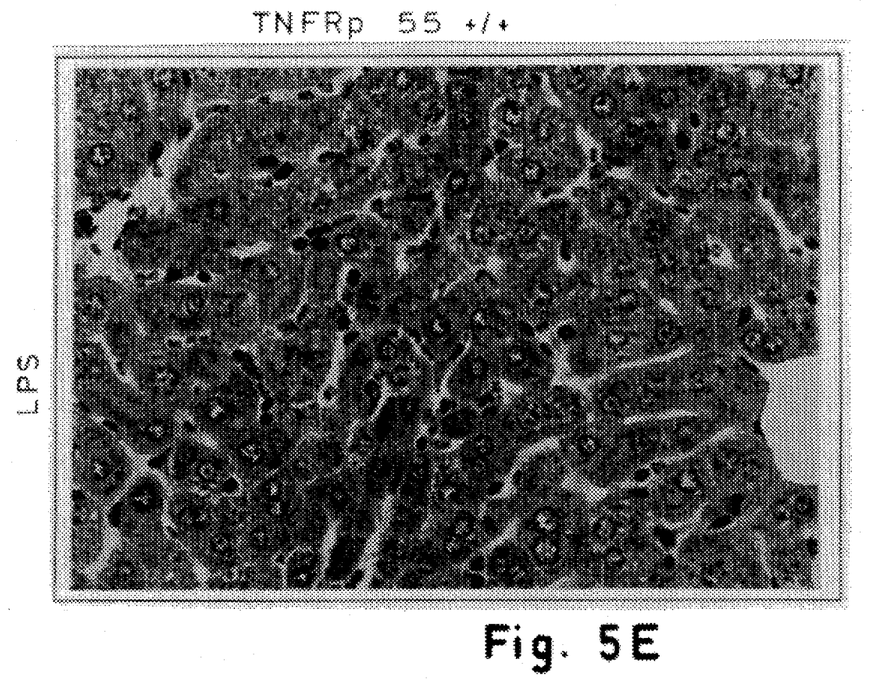
Figure 5F:
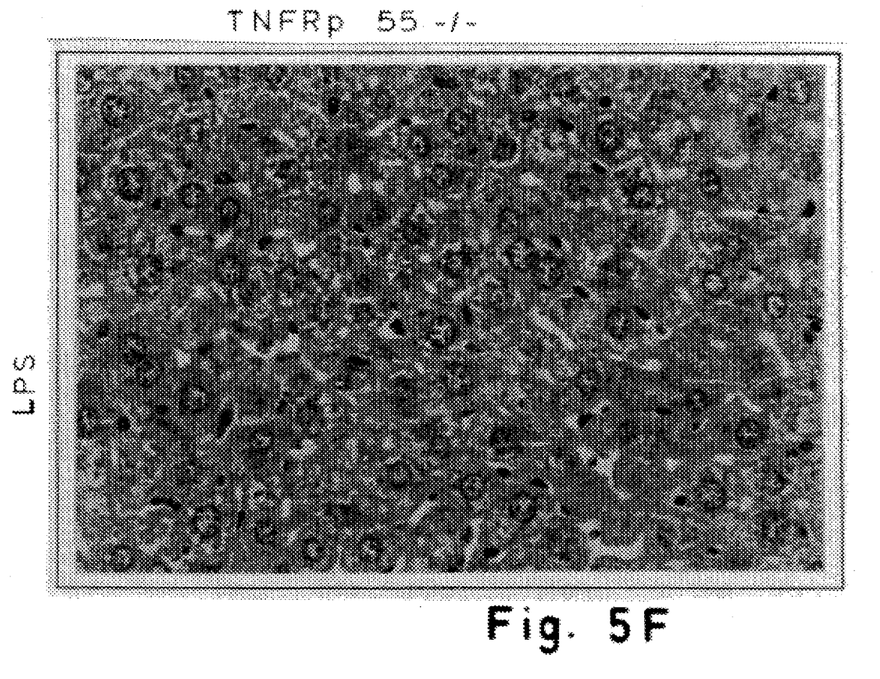
Figure 5G:
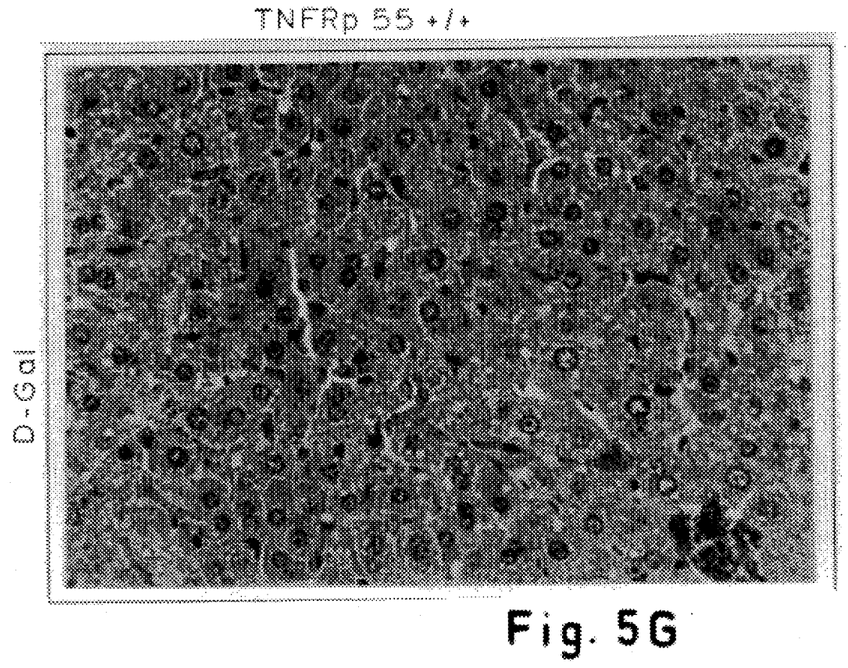
Figure 5H:
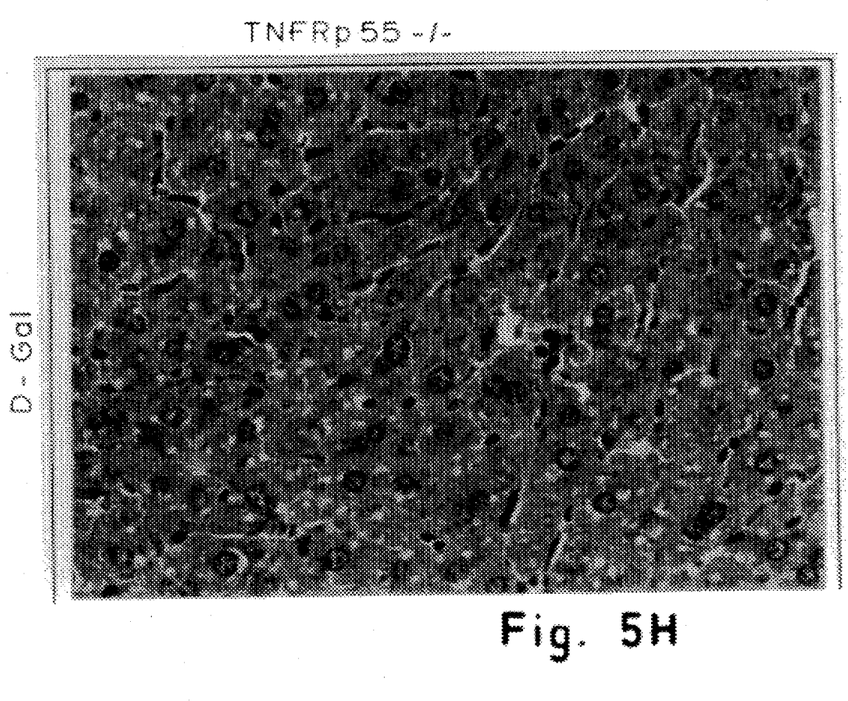

Treatment of mice with a polyclonal antiserum against mouse TNFα starting during pregnancy or at birth leads to atrophy of thymus, spleen and lymph nodes with a decrease of splenic sIgM$^+$ B cells (Kossodo et al., 1992). It also has been reported that the mouse thymus is the only organ where constitutive expression of TNFα can be detected (Giroir et al., 1992). TNFRp55 mutant mice were therefore analysed for development of lymphatic tissues and thymocyte maturation. Examination of TNFRp55–/–, TNFRp55+/–, and wildtype mice revealed no significant differences with regard to numbers of thymocytes, splenocytes, lymph node cells, and bone marrow cells in 4–12 week old mice (data not shown). The number and distribution of thymocyte populations (CD4$^-$8$^-$,CD4$^+$8$^+$,CD4$^+$8$^-$, and CD4$^-$8$^+$) did not differ in TNFRp55+/+ and TNFRp55–/– mice (FIGS. 4A and 4B, respectively). TCR-, HSA-, and CD44- expression in the thymus was also normal (data not shown). The number of B cells in the spleens of TNFRp55–/– animals were not reduced as analyzed by B220 staining (FIGS. 4C and 4D, respectively), and B cell populations in the bone marrow were not changed (data not shown). These results provide evidence that primary and secondary lymphatic organs are phenotypically not altered in TNFRp55–/– mice and suggests that changes observed with antibody treatment against mouse TNFα reflect TNF effects that are putatively mediated via TNFRp75. Blocking of TNFRp55 with antagonistic antibodies has been demonstrated to inhibit apoptosis mediated by TNFα. To address the question if thymocytes lacking TNFRp55 might be resistant to negative selection, clonal deletion of Mls-1$^a$ (MMTV-7)- and I-E- reactive T cells, expressing Vβ6 or Vβ11 TCR β-chains, respectively, was examined. As depicted in Table 1, Vβ6- and Vβ11-positive T cells were efficiently deleted in the peripheral blood of TNFRp55–/– mice, when MMTV-7 or I-E- molecules were present, indicating that clonal deletion of potentially self-reactive T cells is most likely not adversely affected by lack of TNFRp55.

TABLE 1

| TNFRp55 | H-2 | Mls-1 | I-E | Vβ4 | Vβ6 | Vβ11 |
|---|---|---|---|---|---|---|
| +/+ | b/b | b | – | 5.6% | 7.3% | 8.3% |
| +/+ | b/d | a | + | 10.7% | 0.6% | 1.2% |
| –/– | b/b | b | – | 5.6% | 9.9% | 5.9% |
| –/– | b/d | a | + | 9.2% | 0.3% | 1.2% |
| –/– | b/b | a | – | 5.7% | 1.4% | 6.3% |

Protection against endotoxin and superantigen lethality

TNF is a major factor in endotoxin toxicity (Beutler and Cerami, 1988; Beutler and Cerami, 1989; Old, 1988; Paul and Ruddle, 1988) and in superantigen toxicity (Miethke et al., 1992). Antagonizing TNF activity in vivo with anti-TNF antibodies or soluble human TNF receptors has been reported to protect mice from lethality (Tracey et al., 1987; Beutler et al., 1985; Miethke et al., 1992; Ashkenazi et al., 1991). To analyze the role of TNFRp55 in septic shock, TNFRp55–/– mice were challenged with bacterial LPS or staphylococcal enterotoxin B (SEB). At the same time mice were sensitized by injection of D-galactosamine (D-Gal). Co-injection of D-Gal and LPS have been reported to induce a lethal fulminant hepatitis in mice (Beutler and Cerami, 1988; Beutler and Cerami, 1989; Old, 1988; Paul and Ruddle, 1988). Wildtype mice were sensitive to a dosage as low as 0.1 μg LPS/animal, whereas TNFRp55–/– mice were protected even after treatment with 100 μg LPS/animal. Comparably, TNFRp55–/– mice were also protected from lethality after SEB administration (Table 2). In a similar experiment livers of animals were removed 7 hours after LPS and/or D-Gal administration for histopathological analysis. Sections of liver tissue of LPS and D-Gal co-injected TNFRp55+/+ mice showed signs of a fulminant hepatitis with complete necrosis of almost all hepatocytes. In contrast, livers of LPS and D-Gal treated TNFRp55-/- mice showed only signs of an unspecific hepatotoxicity and hepatocytes were not necrotic, the alterations observed were comparable to the pathological findings after D-Gal injection alone (FIGS. 5A-5H). These observations provide evidence for a model where TNFRp55 signalling is required for the establishment of the lethal shock syndrome.

TABLE 2

| D-Gal mg/mouse | LPS ug/mouse | TNFRp55 +/+ dead/group | TNFRp55 -/- dead/group |
|---|---|---|---|
| 20 | — | 0/4 | 0/4 |
| — | 100 | 0/4 | 0/4 |
| 20 | 100 | 6/6 | 0/6 |
| 20 | 10 | 3/3 | 0/3 |
| 20 | 1 | 6/6 | 1/6 |
| 20 | 0.1 | 2/6 | 0/6 |

| D-Gal mg/mouse | SEB ug/mouse | TNFRp55+/+ dead/group | TNFRp55-/- dead/group |
|---|---|---|---|
| | 100 | 0/3 | n.d. |
| 20 | 100 | 3/3 | 0/3 |

Listeria resistance is severely impaired in TNFRp55-/- mice

TNF has been shown to influence host defense mechanisms against a variety of pathogens (1992; Nakane et al., 1988; Nakane, 1992). In order to investigate the immune response of TNFRp55-/- mice against bacterial pathogens, animals were infected with *Listeria monocytogenes* organisms i.v., and mice were monitored for 6 days. TNFRp55-/- mice began to show severe signs of infection after 2 to 3 days and began to succumb to infection after day 3 (Table 3). TNFRp55-/- mice still alive at day 6 showed extremely high titers of alive Listeria in spleen and liver, clearly indicating that TNFRp55-/- mice are severely impaired in clearing Listeria organisms. TNFRp55+/+ mice survived the challenge with Listeria with exhibiting only minor signs of infection at day 2 or 3. At day 6, Listeria titers in TNFRp55+/+ mice were at least 1,000-hold less than titers found in TNFRp55-/- mice (Table 3). These results demonstrate that TNFRp55 is indispensable for elimination of Listeria which also implies that protective immune responses against intracellularly replicating bacteria employ gene products and/or signals which can only be induced by TNFRp55.

TABLE 3

| mouse no. | TNFRp55 | dead | survival | Liver List./g | Spleen List./g |
|---|---|---|---|---|---|
| 1 | +/+ | — | yes | $4.0 \times 10^2$ | $3.2 \times 10^3$ |
| 2 | +/+ | — | yes | $1.6 \times 10^3$ | $2.0 \times 10^2$ |
| 3 | -/- | day 3 | — | | |
| 4 | -/- | day 3 | — | | |
| 5 | -/- | day 4 | — | | |
| 6 | -/- | — | yes | $4.8 \times 10^5$ | $4.4 \times 10^3$ |

Discussion

TNF receptors, upon binding of TNFα or TNFβ, trigger signal cascades that ultimately initiate profound changes in transcriptional programs and metabolism of cells. In order to investigate the functions and to understand the importance of TNF receptors in vivo, the mouse strain with a null mutation of the TNFRp55 gene was produced. Results indicate that it is TNFRp55 that is crucial for host defense against intracellularly replicating bacteria, but also, TNFRp55 mediates the detrimental effects observed in endotoxin and superantigen shock. In the absence of TNFRp55 mouse development appears to be normal and weight and size of mutant animals are not reduced or increased. The data indicate that TNFRp75 cannot substitute for TNFRp55 and suggest that functional programs triggered by each receptor are different. It might well be the case that TNFRp75 is involved in homeostasis of body weight.

TNF mRNA has been detected in mouse embryos, fetal thymus and spleen (Giroir et al., 1992; Oshawa and Natori, 1989). Antibody treatment in newborn mice with a polyclonal rabbit anti-mouse TNFα antibody led to transient growth retardation and a marked atrophy of thymus, spleen, and lymph nodes with lymphopenia and a reduction of B cells (Kossodo et al., 1992). TNFRp55-/- mice exhibit normal organ sizes of lymphatic tissues, and lymphocyte populations are not significantly altered when compared to control littermates. These data might suggest that TNF actions leading to the observed alterations in antibody treated animals are mediated via TNFRp75 transduced signal events.

The thymus is the only organ constitutively expressing TNF in the adult mouse. It has been shown that mature and immature thymocytes as well as dendritic cells express TNF. Therefore, it has been suggested that TNF may participate in the establishment of self-tolerance by triggering apoptosis of self-reactive thymocytes. Apoptosis is thought to be mediated mainly via TNFRp55. However, in TNFRp55-/- mice clonal deletion of potentially autoreactive thymocytes is not impaired. Whether TNF is involved thymic development and thymocyte apoptosis via TNFRp75 transduced signals, or whether thymocyte apoptosis is independent from TNF actions, remains to be elucidated.

It has been demonstrated, that TNF stimulates the production of DAG by a PC-specific phospholipase. DAG activates an acidic Sphingomyelinase which leads to sphingomyelin breakdown and the formation of ceramide which is coupled to activation of NF-κB (Vassalli, 1992). The induction of NF-κB was shown to be dependent upon TNFRp55 expression (Wiegmann et al., 1992). Spleen cells from mice without TNFRp55 cannot activate NF-κB, indicating that TNFRp55 signaling is completely abrogated in TNFRp55 mutant mice.

It has been reported that TNF is an important mediator in endotoxin and superantigen shock (Morrison and Ryan, 1987; Tracey et al., 1986; Miethke et al., 1992). Endotoxin triggers TNF release from macrophages, kidney, heart, islets of Langerhans, spleen, lung, fallopian tubes, and uterus, but not from liver and brain (Giroir et al., 1992), whereas T cells are the source of TNF in response to superantigen (Miethke et al., 1992). After sensitization with D-galactosamine, mice readily die from endotoxin and superantigen-induced TNF release, probably by development of a fulminant hepatitis (Thomas and Capecchi, 1987; Beutler and Cerami, 1989; Old, 1988; Paul and Ruddle, 1988). As shown herein that TNFRp55 mutant mice are protected from lethality of TNF actions, and the hepatocytes from TNFRp55-/-, in contrast to TNFRp55+/+, animals do not undergo necrosis. C3H/HeJ mice have been found to be naturally resistant against LPS administration, and the mutation ($Lps^d$) involved into resistance has been mapped to mouse chromosome 4, with a dominant or codominant inheritance pattern (Vogel, 1992). B cells from CBA/CaHN-xid/J mice do not respond to stimulation with LPS. This B-cell defect (xid) has been mapped to the X-chromosome and has a recessive inheritance pattern (Vogel, 1992). Both mutations are different from the mutation of the TNFRp55 which maps to mouse chromosome 6 (Goodwin et al., 1991) and cannot account for the LPS resistance in TNFRp55–/– mice. Further studies have to determine whether the PC-PLC/NF-κB linked, the PKC linked, or both together deliver the signal(s) leading to necrosis of cells after TNFRp55 stimulation.

It has been previously shown that Listeria infection in mice is exacerbated with anti-TNF treatment (Nakane, 1992) and that administration of TNF can protect mice against otherwise lethal infections with Listeria (Nakane, 1992). Interestingly, TNFRp55–/– mice are extremely susceptible to Listeria and easily succumb to infection. This demonstrates that without TNFRp55 replication of Listeria cannot be controlled in vivo. This suggests that metabolic changes and transcription of genes controlled by TNFRp55 are crucial for development of a host defense against intracellular replicating bacteria.

The data presented herein indicate that TNFRp55 mediates important functions in vivo. Complete abrogation of signals of TNFRp55 can be beneficial for the outcome of shock syndromes but can simultaneously prove extremely harmful by destruction of host defense against pathogens. It remains to be elucidated whether these effects can be dissected by being transduced by different signal cascades triggered by TNFRp55.

Experimental Procedures
Cells

D3 embryonic stem (ES) cells from 129/Sv mice were maintained in the undifferentiated state by growth on a feeder layer of mitomycin C-treated embryonic fibroblasts in culture medium (D-MEM) supplemented with leukemia inhibitory factor, 15% FCS, L-glutamine, and β-mercaptoethanol.

Generation of TNFRp55-deficient mice

The murine cDNA for TNFRp55 was cloned from a mouse T cell cDNA library in lambda ZAP$^R$II (Stratagene) using the rat TNFRp75 cDNA (Himmler et al., 1990). Murine TNFRp55 cDNA clone 11 was partially sequenced and used for screening of a mouse genomic library (partial MboI digest of Balb/C genomic DNA in EMBL3). Genomic clones were mapped and partially sequenced. A 3.2 kB genomic fragment (gTR55) containing 3 exons covering together bp 515 to 748 of the cDNA sequence was used to construct the targeting vector. The 1.2 kB XhoI-SalI fragment of pMC1polA was subcloned into pBluescript and reexcised by BamHI. Subsequently this neo-casette was ligated into the BglII restriction site of gTR55, disrupting the coding sequence at bp 535 (corresponding to cDNA) to obtain the targeting vector gTR55neoA. D3 ES cells were transfected with 20 ug linearized gTR55neoA DNA/5×10$^6$ ES cells by electroporation (Bio-Rad Gene Pulser, 340V, 250 uF). G418 selection (300 ug/ml) was applied 48 hours after transfection and G418-resistant colonies were obtained after 10 days of selection. PCR screening for homologous recombination was carried out as described (Fung-Leung et al., 1191). A primer specific for the HSV-TK promoter in the neomycin resistance gene (5'-attcggcaatgacaagacgctgg-3') and an outside primer specific for the TNFRp55 gene (5'-ttgccagacgtttgctgcaagcg-3') upstream of the construct were used in PCR. Homologous recombination was subsequently confirmed by EcoRI digestion of genomic DNA and hybridization with probe A (FIG. 1A). Chimeric mice were produced by injection of ES cells into 3.5 days old blastocyts as described (Thompson et al., 1989; Fung-Leung et al., 1191). The contribution of ES cells to the germline of chimeric mice was assessed by breeding with (C57BL/6× DBA/2)F1 mice and screening for agouti offspring. Germline transmission of the TNFRp55 mutation was confirmed by Southern analysis of the tail DNA, and mice heterozygous for the mutant gene were interbred to homozygosity.

For investigation of clonal deletion, F2 homozygous mice with H-2 haplotypes b/d and b/b were interbred. Offspring were typed for H-2 using flow cytometry. Mice were typed for Mls-1$^a$ by Southern blot, analysis for MMTV-7 integration, which was determined by the presence of an 11.7 kB band in blots of EcoRI digested genomic DNA probed with an MMTV env probe.

Production of mAb against mouse TNFRp75

A partial TNFRp75 cDNA clone spanning bp 68 to 1102 (Lewis et al., 1991) was obtained by PCR with a primer set (5'-atgggatcccggtcttcgaactgcagctg-3' and 5'-ctagaattcatgactcttgcttgggatgg-3') containing engineered BamHI and EcoRI restriction sites, respectively, for in frame subcloning into the procaryotic expression vector pGEX3X (Pharmacia). pGEXTR75 was transfected into DH5α and fusion protein was purified after induction of cultures with IPTG. 5 mg of fusion protein was injected i.p. into 2 rats for 5 times. Hybridoma fusion was performed, and hybridoma supernatants were differentially screened using an ELISA system with plates coated with the glutathione-TNFRp75 fusion protein or glutathione alone.

Radioligand binding assay

Spleen cells of mice were cultured in the presence of ConA (8 ug/ml) in Iscove's modified D-MEM supplemented with 10% FCS, L-glutamine and β-mercaptoethanol. Human and mouse TNFα were labelled with $^{125}$I. For determination of the total amount of cell-associated $^{125}$I-TNF, cells were incubated for 1 hour at 0° C. with 20 ng/ml of $^{125}$I-TNF to saturate cell surface TNF receptors. Cells were layered on top of a discontinuous gradient consisting of a) 0.5 ml of culture medium supplemented with 20% Ficoll; b) 3 ml phosphate buffered saline (pH7.3) 10% Ficoll; and c) 0.5 ml of culture medium containing 5% Ficoll. Cells were centrifuged for 10 min at 50×g, and the radioactivity of cell pellets was determined. Nonspecific binding was measured in the presence of excess unlabelled TNF and was subtracted from the values obtained in the absence of unlabelled TNF. Blocking of TNF binding was performed by incubation of cells with rat anti-mouse TNFRp75 mAb KaTR7 before addition of radiolabelled TNF.

Nuclear Extract Preparation and Electrophoretic Mobility Shift Assays

For preparation of nuclear extracts, 5×10$^6$ cells in 5 ml of culture medium were left untreated or stimulated for 20 min with recombinant human or mouse TNF (10 ng/ml). Cell cultures were washed twice with ice-cold phosphate-buffered saline and resuspended in 400 ul of buffer A (10 mM HEPES [ph 7.8], 10 mM KCl, 0.1 mM EDTA, 0.1 mM EGTA, 1 mM dithiothreitol, and 1 mM phenylmethylsulfonyl fluoride). After 15 min, Nonidet P-40 was added to a final concentration of 0.6%. Nuclei were pelletted and resuspended in 50 ul of buffer C (20 mM HEPES [pH 7.9], 0.4M NaCl, 1 mM EDTA, and 1 mM EGTA). After 30 min at 4° C., lysates were centrifuged and supernatants containing the nuclear proteins were transferred to new vials. The protein concentration of extracts was measured using a bicinchoninic acid assay (Pierce) with bovine serum albumin as standard.

Electrophoretic mobility shift assays were performed by incubation 6 ug of nuclear extract with 4 ug of poly(dI-dC) (Pharmacia) in a binding buffer (5 nM HEPES [pH 7.8], 5 nM $MgCl_2$, 50 mM KCl, 0.5 mM dithioreitol, 10% glycerol [20 ul final volume]) for 20 min at room temperature. Then end-labeled double-stranded oligonucleotide probe ($1 \times 10^4$ to $5 \times 10^4$ cpm) was added and the reaction mixture was incubated for 7 min. The samples were separated by native polyacrylamide gel electrophoresis in low ionic strength buffer (0.25×Tris-borate-EDTA).

Flow cytometric analysis

The following monoclonal antibodies were used: CD4-FITC (Pharmingen, clone: RM4-5), CD8-PE (Pharmingen, clone: 53-6.7), B220 (Pharmingen, clone: RA3-6B2) and Thy-1.2-PE (Pharmingen, clone:53-2.1), V$\beta$4-FITC, V$\beta$6-FITC, V$\beta$11-FITC.

Thymus, spleen and lymph node suspension were prepared according to standard procedures. Cells ($5 \times 10^5$) were incubated in staining buffer (2% serum bovine albumine, 0.1% $NaN_3$ in phosphate buffered saline) with monoclonal antibodies for 30 min. at 4° C. Cells were washed twice in staining buffer and resuspended in phosphate-buffered saline containing 1% paraformaldehyde. 10,000 viable cells were analyzed using a FACScan flow cytometer (Becton-Dickinson).

Endotoxin and Superantigen-shock

LPS (L-3129), Staphylococcal enterotoxin B (S4881) and D-Galactosamine (G1639) were purchased from Sigma. Mice were injected with indicated amounts of reagents dissolved in 0.1 ml of phosphate-buffered saline. Tissues for histology were removed and transferred into 10% formalin solution. Sections were stained with hematoxylin and eosin. Slides were photographed using a Leitz photomicroscope.

Listeria infection

Mice were i.v. injected with live *Listeria monocytogenes*. Animals were sacrificed at day 6 and titers of Listeria in spleen and liver were determined. Liver and spleen were homogenized in 2 ml phosphate-buffered saline and serial log-dilutions of homogenates were plated on Columbia-agar plates.

Deposits

The ES cell line having the disrupted TNFRp55 gene has been deposited in the American Type Culture Collection, Rockville, Md., and given ATCC Accession No. CRL 11379.

REFERENCES

1. Ashkenazi, A., Marsters, S. A., Capon, D. J., Chamow, S. M., Figari, I. S., Pennica, D., Goeddel, D. V., Palladino, M. A., and Smith, D. H. (1991). Protection against endotoxic shock by a tumor necrosis factor receptor immunoadhesin. Proceedings of the National Academy of Sciences of the United States of America 88, 10535–10539.

2. Baeuerle, P. A. (1991). The inducible transcription factor NF-kappaB:regulation by distinct protein subunits. Biochim. Biophys. Acta 1072, 63–80.

3. Beutler, B. and Cerami, A. (1988). Tumor necrosis, cachexia, shock, and inflammation: a common mediator. Annu. Rev. Biochem. 57, 505–518.

4. Beutler, B. and Cerami, A. (1989). The biology of cachectin/TNF—a primary mediator of the host response. Annu. Rev. Immunol. 7, 625–655.

5. Beutler, B., Milsark, I. W., and Cerami, A. C. (1985). Passive immunization against cachectin/tumor necrosis factor protects mice from lethal effect of endotoxin. Science 229, 869–871.

6. Bradley, A., Evans, M., Kaufman, M. H., and Robertson, E. (1984). Formation of germ-line chimaeras from embryo-derived teratocarcinoma cell lines. Nature 309, 255–256.

7. Bradley, A. and Robertson, E. (1986). Embryo-derived stem cells: a tool for elucidating the developmental genetics of the mouse. Curr. Top. Dev. Biol. 20, 357–371.

8. Fung-Leung, W.-P., Schilham, M., Rahemtulla, A., Kundig, T., Vollenweider, M., Potter, J., van Ewijk, W., and Mak, T. W. (1991). CD8 is needed for development of cytotoxic T cells but not helper T cells. Cell 65, 443–449.

9. Giroir, B. P., Brown, T., and Beutler, B. (1992). Constitutive synthesis of tumor necrosis factor in the thymus. Proc. Natl. Acad. Sci. USA 89, 4864–4868.

10. Giroir, B. P., Johnson, J. H., Brown, T., Allen, G. L., and Beutler, B. (1992). The tissue distribution of tumor necrosis factor biosynthesis during endotoxemia. J. Clin. Invest. 90, 693–698.

11. Goodwin, R. G., Anderson, D., Jerzy, R., Davis, T., Brannan, C. I., Copeland, N. G., Jenkins, N. A., and Smith, C. A. (1991). Molecular cloning and expression of the type 1 and type 2 murine receptors for tumor necrosis factor. Molecular & Cellular Biology 11, 3020–3026.

12. Gray, P. W., Barrett, K., Chantry, D., Turner, M., and Feldmann, M. (1990). Cloning of human tumor necrosis factor (TNF) receptor cDNA and expression of recombinant soluble TNF-binding protein. Proc. Natl. Acad. Sci. U.S.A. 87, 7380–7384.

13. Himmler, A., Maurer-Fogy, I., Kronke, M., and et al., (1990). Molecular cloning and expression of human and rat tumor necrosis factor receptor chain (p60) and its soluble derivative, tumor necrosis factor binding protein. DNA Cell Biol. 9, 705–715.

14. Kossodo, S.de, Grau, G. E., Daneva, T., Pointaire, P., Fossati, L., Ody, C., Zapf, J., Piguet, P.-F., Galliard, R. C., and Vassalli, P. (1992). Tumor necrosis factor alpha is involved in mouse growth and lymphoid tissue development. J. Exp. Med. 176, 1259–1264.

15. Lewis, M., Tartaglia, L. A., Lee, A., Bennett, G. L., Rice, G. C., Wong, G. H., Chen, E. Y., and Goeddel, D. V. (1991). Cloning and expression of cDNAs for two distinct murine tumor necrosis factor receptors demonstrate one receptor is species specific. Proceedings of the National Academy of Sciences of the United States of America 88, 2830–2834.

16. Loetscher, H., Pan, Y. C., Lahm, H. W., Gentz, R., Brockhaus, M., Tabuchi, H., and Lesslauer, W. (1990). Molecular cloning and expression of the human 55 kd tumor necrosis factor receptor. Cell 61, 351–359.

17. Mallett, S. and Barclay, A. N. (1991). A new superfamily of cell surface proteins related to the nerve growth factor receptor. Immunol. Today 7, 220–223.

18. Miethke, T., Wahl, C., Heeg, K., Echtenacher, B., Krammer, P. H., and Wagner, H. (1992). T cell-mediated lethal shock triggered in mice by the superantigen staphylococcal enterotoxin B: critical role of tumor necrosis factor. J. Exp. Med. 175, 91–98.

19. Morrison, D. C. and Ryan, J. L. (1987). Endotoxins and disease mechanisms. Annu. Rev. Med. 38, 417.

20. Nakane, A. (1992). TNF in Listeriosis. In Tumor necrosis factors:The molecules and their emerging role in Medicine. B. Beutler, ed. (New York: Raven Press, Ltd.), pp. 285–292.

21. Nakane, A., Minigawa, T., and Kato, K. (1988). Endogenous tumor necrosis factor (cachectin) is essential to host resistance against Listeria monocytogenes infection. Infect. Immun. 56, 731–740.

22. Nophar, Y., Kemper, O., Brakebusch, C., Englemann, H., Zwang, R., Aderka, D., Holtmann, H., and Wallach, D.

(1990). Soluble forms of tumor necrosis factor receptors (TNF-Rs). The cDNA for the type I TNF-R, cloned using amino acid sequence data of its soluble form, encodes both the cell surface and a soluble form of the receptor. EMBO J. 9, 3269–3278.

23. Old, L. J. (1988). Tumor necrosis factor. Sci. Am. 258, 59–60, 69–75.

24. Oshawa, T. and Natori, S. (1989). Expression of tumor necrosis factor at a specific stage of mouse embryos. Dev. Biol. 135, 459.

25. Paul, N. L. and Ruddle, N. H. (1988). Lymphotoxin. Ann. Rev. Immunol. 6, 407–438.

26. Schall, T. J., Lewis, M., Koller, K. J., Lee, A., Rice, G. C., Wong, G. H., Gatanaga, T., Granger, G. A., Lentz, R., Raab, H., and et al, (1990). Molecular cloning and expression of a receptor for human tumor necrosis factor. Cell 61, 361–370.

27. Schutze, S., Potthoff, K., Machleidt, T., Berkovic, D., Wiegmann, K., and Kronke, M. (1992). TNF activates NF-kappaB by phosphatidylcholine-specific phospholipase C-induced "acidic" sphingomyelin breakdown. Cell 71, 765–776.

28. Smith, C. A., Davis, T., Anderson, D., Solam, L., Beckmann, M. P., Jerzy, R., Dower, S. K., Cosman, D., and Goodwin, R. G. (1990). A receptor for tumor necrosis factor defines an unusual family of cellular and viral proteins. Science 248, 1019–1023.

29. Tartaglia, L. A. and Goeddel, D. V. (1992). Two TNF receptors. Immunol. Today 13, 151–153.

30. Thoma, B., Grell, M., Pfizenmaier, K., and Scheurich, P. (1990). Identification of a 60-kD tumor necrosis factor (TNF) receptor as the major signal transducing component in TNF responses. J. Exp. Med. 172, 1019–1023.

31. Thomas, K. R. and Capecchi, M. R. (1987). Site-directed mutagenesis by gene targeting in mouse embryo-derived stem cells. Cell 51, 503–512.

32. Thompson, S., Clarke, A. R., Pow, A. M., Hooper, M. L., and Melton, D. W. (1989). Germ line transmission and expression of a corrected HPRT gene produced by gene targeting in embryonic stem cells. Cell 56, 313–321.

33. Tracey, K. J., Beutler, B., Lowry, S. F., Merryweather, J., Wolpe, S., Milsark, I. W., Hariri, R. J., Fahey, T. J., Zentella, A., Albert, J. D., and et al, (1986). Shock and tissue injury induced by recombinant human cachectin. Science 234, 470–474.

34. Tracey, K. J., Fong, Y., Hesse, D. G., Manogue, K. R., Lee, A. T., Kuo, G. C., Lowry, S. F., and Cerami, A. (1987). Anti-cachectin/TNF monoclonal antibodies prevent septic shock during lethal bacteraemia. Nature 330, 662.

35. Vassalli, P. (1992). The pathophysiology of tumor necrosis factor. Annu. Rev. Immunol. 10, 411.

36. Vogel, S. N. (1992). The lps gene. In Tumor necrosis factors: The molecules and their emerging role in medicine. B. Beutler, ed. (New York: Raven Press,Ltd.), pp. 485–513.

37. Wiegmann, K., Schutze, S., Kampen, E., Himmler, A., Machleidt, T., and Kronke, M. (1992). Human 55-kDa receptor for tumor necrosis factor coupled to signal transduction cascades. J. Biol. Chem. 267,17997–18001.

I claim:

1. A mutant mouse comprising a TNFRp55 gone having a disruption in as least one exon thereof, wherein (1) said disruption has been introduced into the genome of said mouse by homologous recombination in an embryonic stem cell, and (2) said disruption provides a null mutation which results in no expression of tumor necrosis factor receptor p55 (TNFRp55) by said mouse, and further wherein said mouse lacks the ability to bind human TNFα and is more susceptible to infection by *Listeria monocytogenes* than a mouse lacking said disruption.

2. The mouse of claim 1, wherein said disruption by homologous recombination is made by inserting a marker sequence into an exon of the TNFRp55 gene thereby disrupting its coding sequence.

3. A mouse as claimed in claim 2, wherein a SalI-BamHI DNA fragment containing three exons of a 3.2 kB fragment of the TNFRp55 gene is used as a construct, and the coding sequence of an exon of gTR55 having a BglII restriction enzyme site is disrupted by inserting a marker sequence for neomycin resistance into the BglII restriction enzyme site of said exon.

4. The mouse as claimed in claim 3, wherein the construct is inserted into embryonic stem cells by electroporation, and neomycin resistant colonies arising therefrom are screened for the homologous recombination event by cellular DNA screening using the polymerase chain reaction.

5. The mouse of claim 1, wherein the number and distribution of $CD4^-8^-$, $CD4^+8^+$, $CD4^+8^{31}$, and $CD4^-8^+$ thymocytes in the thymus of the mutant mouse do not differ from the number and distribution of said thymocytes found in the thymus of a wild type mouse that lacks a disruption in the TNFRp55 gene.

6. A mouse as claimed in claim 5, wherein clonal deletion of self-reactive T cells is not altered by the mutation.

7. The embryonic stem (ES) cell line having a disrupted TNFRp55 gene, ATCC Accession No. CRL 11379.

* * * * *

UNITED STATES PATENT AND TRADEMARK OFFICE
CERTIFICATE OF CORRECTION

PATENT NO. : 5,684,222
DATED : November 4, 1997
INVENTOR(S) : Mak

It is certified that error appears in the above-identified patent and that said Letters Patent is hereby corrected as shown below:

Title page,
Item [54], after "TNFRP55", insert -- GENE --, therefor.

Column 5,
Line 46, please delete "1000-hold" and insert -- 1000-fold --, therefor.

Column 12,
Line 13, please delete "gone" and insert -- gene --, therefor.
Line 40, please delete "$CD4^+8^{31}$" and insert -- $CD4^+8^-$ --, therefor.

Signed and Sealed this

Twenty-first Day of May, 2002

Attest:

Attesting Officer

JAMES E. ROGAN
*Director of the United States Patent and Trademark Office*